United States Patent
Kozloski et al.

(10) Patent No.: US 10,165,979 B2
(45) Date of Patent: *Jan. 1, 2019

(54) HELMET HAVING A CUMULATIVE CONCUSSION INDICATOR

(71) Applicant: INTERNATIONAL BUSINESS MACHINES CORPORATION, Armonk, NY (US)

(72) Inventors: James R. Kozloski, New Fairfield, CT (US); Mark C. H. Lamorey, Williston, VT (US); Clifford A. Pickover, Yorktown Heights, NY (US); John J. Rice, Mohegan Lake, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 231 days.

This patent is subject to a terminal disclaimer.

(21) Appl. No.: 14/745,498

(22) Filed: Jun. 22, 2015

(65) Prior Publication Data

US 2016/0331319 A1    Nov. 17, 2016

Related U.S. Application Data

(63) Continuation of application No. 14/709,563, filed on May 12, 2015.

(51) Int. Cl.
*A61B 5/00* (2006.01)
*A42B 3/04* (2006.01)
(Continued)

(52) U.S. Cl.
CPC ............ *A61B 5/6803* (2013.01); *A42B 3/046* (2013.01); *A61B 5/0022* (2013.01);
(Continued)

(58) Field of Classification Search
CPC .................................................. A61B 5/6803
See application file for complete search history.

(56) References Cited

U.S. PATENT DOCUMENTS

2007/0050715 A1* 3/2007 Behar ................... A61B 5/0002
715/706
2011/0181419 A1* 7/2011 Mack ..................... A42B 3/046
340/573.1
(Continued)

OTHER PUBLICATIONS

List of IBM Patents or Patent Applications Treated as Related—Date Filed: Aug. 20, 2015; 2 pages.
(Continued)

*Primary Examiner* — Sean Dougherty
*Assistant Examiner* — Nicholas E Kolderman
(74) *Attorney, Agent, or Firm* — Cantor Colburn LLP; Vazken Alexanian

(57) ABSTRACT

Embodiments include methods, systems and computer program products for monitoring a user of a helmet for cumulative concussions. Aspects include monitoring one or more sensors in the helmet and receiving an output from the one or more sensors corresponding to an impact experienced by the helmet. Aspects also include calculating a cumulative concussion score based on the output of the one or more sensors and displaying an indication of the cumulative concussion score via an indicator on the helmet.

4 Claims, 5 Drawing Sheets

(51) Int. Cl.
G06F 19/00 (2018.01)
G16H 40/67 (2018.01)
(52) U.S. Cl.
CPC .......... *A61B 5/4064* (2013.01); *A61B 5/4076* (2013.01); *A61B 5/7282* (2013.01); *A61B 5/747* (2013.01); *G06F 19/00* (2013.01); *G16H 40/67* (2018.01); *A61B 5/7275* (2013.01); *A61B 5/744* (2013.01); *A61B 5/746* (2013.01); *A61B 5/7445* (2013.01); *A61B 2503/22* (2013.01); *A61B 2562/0219* (2013.01)

(56) References Cited

U.S. PATENT DOCUMENTS

| | | | | |
|---|---|---|---|---|
| 2011/0181420 | A1* | 7/2011 | Mack | A42B 3/046 340/573.1 |
| 2013/0110415 | A1* | 5/2013 | Davis | A42B 3/046 702/41 |
| 2013/0271602 | A1* | 10/2013 | Bentley | H04N 7/18 348/143 |
| 2015/0037771 | A1* | 2/2015 | Kaleal, III | G09B 5/02 434/257 |
| 2015/0375083 | A1* | 12/2015 | Stelfox | G01S 5/0263 700/91 |

OTHER PUBLICATIONS

U.S. Appl. No. 14/664,987, filed Mar. 23, 2015; Entitled: Monitoring a Person for Indications of a Brain Injury.
U.S. Appl. No. 14/664,989, filed Mar. 23, 2015; Entitled: Monitoring a Person for Indications of a Brain Injury.
U.S. Appl. No. 14/664,991, filed Mar. 23, 2015; Entitled: Monitoring a Person for Indications of a Brain Injury.
U.S. Appl. No. 14/709,563, filed May 12, 2015; Entitled: "Helmet Having a Cumulative Concussion Indicator".
U.S. Appl. No. 14/709,564, filed May 12, 2015; Entitled: "Monitoring Impacts Between Individuals for Concussion Analysis".
U.S. Appl. No. 14/709,568, filed May 12, 2015; Entitled: "Helmet Having an Embedded Cooling Array".
U.S. Appl. No. 14/709,570, filed May 12, 2015; Entitled: "Mouthguard for Analysis of Biomarkers for Traumatic Brain Injury".
U.S. Appl. No. 14/709,572, filed May 12, 2015; Entitled: "Suggesting Adjustments to a Helmet Based on Analysis of Play".
U.S. Appl. No. 14/709,574, filed May 12, 2015; Entitled: "Automatic Adjustment of Helmet Parameters Based on a Category of Play".
U.S. Appl. No. 14/709,575, filed May 12, 2015; Entitled: "Detection of a Traumatic Brain Injury with a Mobile Device".
U.S. Appl. No. 14/744,061, filed Jun. 19, 2015; Entitled: Monitoring a Person for Indications of a Brain Injury.
U.S. Appl. No. 14/744,063, filed Jun. 19, 2015; Entitled: Monitoring a Person for Indications of a Brain Injury.
U.S. Appl. No. 14/744,064, filed Jun. 19, 2015; Entitled: Monitoring a Person for Indications of a Brain Injury.
U.S. Appl. No. 14/745,491, filed Jun. 22, 2015; Entitled: "Automatic Adjustment of Helmet Parameters Based on a Category of Play".
U.S. Appl. No. 14/745,492, filed Jun. 22, 2015; Entitled: "Detection of a Traumatic Brain Injury with a Mobile Device".
U.S. Appl. No. 14/745,493, filed Jun. 22, 2015; Entitled: "Suggesting Adjustments to a Helmet Based on Analysis of Play".
U.S. Appl. No. 14/745,494, filed Jun. 22, 2015; Entitled: "Mouthguard for Analysis of Biomarkers for Traumatic Brain Injury".
U.S. Appl. No. 14/745,495, filed Jun. 22, 2015; Entitled: "Helmet Having an Embedded Cooling Array".
U.S. Appl. No. 14/745,497, filed Jun. 22, 2015; Entitled: "Monitoring Impacts Between Individuals for Concussion Analysis".

* cited by examiner

HELMET HAVING A CUMULATIVE CONCUSSION INDICATOR

DOMESTIC PRIORITY

This application is a continuation of U.S. application Ser. No. 14/709,563; Filed: May 12, 2015; which is related to U.S. application Ser. No. 14/709,575; Filed: May 12, 2015; U.S. application Ser. No. 14/709,574; Filed: May 12, 2015; U.S. application Ser. No. 14/709,572; Filed: May 12, 2015; U.S. application Ser. No. 14/709,570; Filed: May 12, 2015; U.S. application Ser. No. 14/709,568; Filed: May 12, 2015; U.S. application Ser. No. 14/709,564; Filed: May 12, 2015; U.S. application Ser. No. 14/664,987; Filed Mar. 23, 2015; U.S. application Ser. No. 14/664,989; Filed: Mar. 23, 2015; and U.S. application Ser. No. 14/664,991; Filed: Mar. 23, 2015; the contents of each of which are herein incorporated by reference in their entirety.

BACKGROUND

The present disclosure relates to monitoring an individual for cumulative concussions, and more specifically, to methods, systems and computer program products for using sensors in a helmet to monitor a user for cumulative concussions.

Generally speaking, safety is a primary concern for both users of helmets and manufacturers of helmets. Helmets are used by individuals that participate in activities that have risk of head trauma, such as the area of sports, biking, motorcycling, etc. While helmets have traditionally been used to provide protection from blunt force trauma to the head, an increased awareness of concussion causing forces has motivated a need for advances in helmet technology to provide increased protection against concussions. A concussion is a type of traumatic brain injury that is caused by a blow to the head that shakes the brain inside the skull due to linear or rotational accelerations. Recently, research has linked concussions to a range of health problems, from depression to Alzheimer's, along with a range of brain injuries. Unlike severe traumatic brain injuries, which result in lesions or bleeding inside the brain and are detectable using standard medical imaging, a concussion is often invisible in brain tissue, and therefore only detectable by means of a cognitive change, where that change is measurable by changes to brain tissue actions, either neurophysiological or through muscle actions caused by the brain and the muscles resulting effects on the environment, for example, speech sounds.

Currently available helmets use accelerometers to measure the forces that the helmet, and therefore the head of the user, experiences. These accelerometers can be used to indicate when a force experienced by a helmet exceeds a threshold level that indicates that the impact was sufficiently large enough to cause a traumatic brain injury to the user. However, currently available helmets are not configured to track the cumulative effects of impacts that fall below the threshold used to indicate possible traumatic brain injuries to the user.

SUMMARY

In accordance with an embodiment, a method for monitoring a user of a helmet for cumulative concussions includes monitoring one or more sensors in the helmet and receiving an output from the one or more sensors corresponding to an impact experienced by the helmet. The method also includes calculating a cumulative concussion score based on the output of the one or more sensors and displaying an indication of the cumulative concussion score via an indicator on the helmet.

In accordance with another embodiment, a helmet for monitoring a user of for cumulative concussions includes a processor and a camera. The processor is configured to perform a method that includes monitoring one or more sensors in the helmet and receiving an output from the one or more sensors corresponding to an impact experienced by the helmet. The method also includes calculating a cumulative concussion score based on the output of the one or more sensors and displaying an indication of the cumulative concussion score via an indicator on the helmet.

In accordance with a further embodiment, a computer program product for monitoring a user of a helmet for cumulative concussions includes a non-transitory storage medium readable by a processing circuit and storing instructions for execution by the processing circuit for performing a method. The method includes monitoring one or more sensors in the helmet and receiving an output from the one or more sensors corresponding to an impact experienced by the helmet. The method also includes calculating a cumulative concussion score based on the output of the one or more sensors and displaying an indication of the cumulative concussion score via an indicator on the helmet.

BRIEF DESCRIPTION OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

DETAILED DESCRIPTION

In accordance with exemplary embodiments of the disclosure, methods, systems and computer program products for using sensors in a helmet to monitor a user for indications of cumulative concussions are provided. In exemplary embodiments, the sensors may include one or more of accelerometers, gyroscopes, or the like. In general, the outputs of the sensors are used to monitor the severity of impacts suffered by the user. In exemplary embodiments, the severity of the impact may include the amount of acceleration and or rotation experienced by the helmet. The helmet includes a memory used to store the data received from the sensors and a processor configured to calculate a cumulative concussion score based on the stored data. In exemplary embodiments, the helmet also includes an indicator that is controlled by the processor and that is configured to provide a visual indication of the cumulative concussion score. For example, the indicator may be a light emitting diode (LED) that is configured to display different colors based on the value of the cumulative concussion score.

Figure 1:
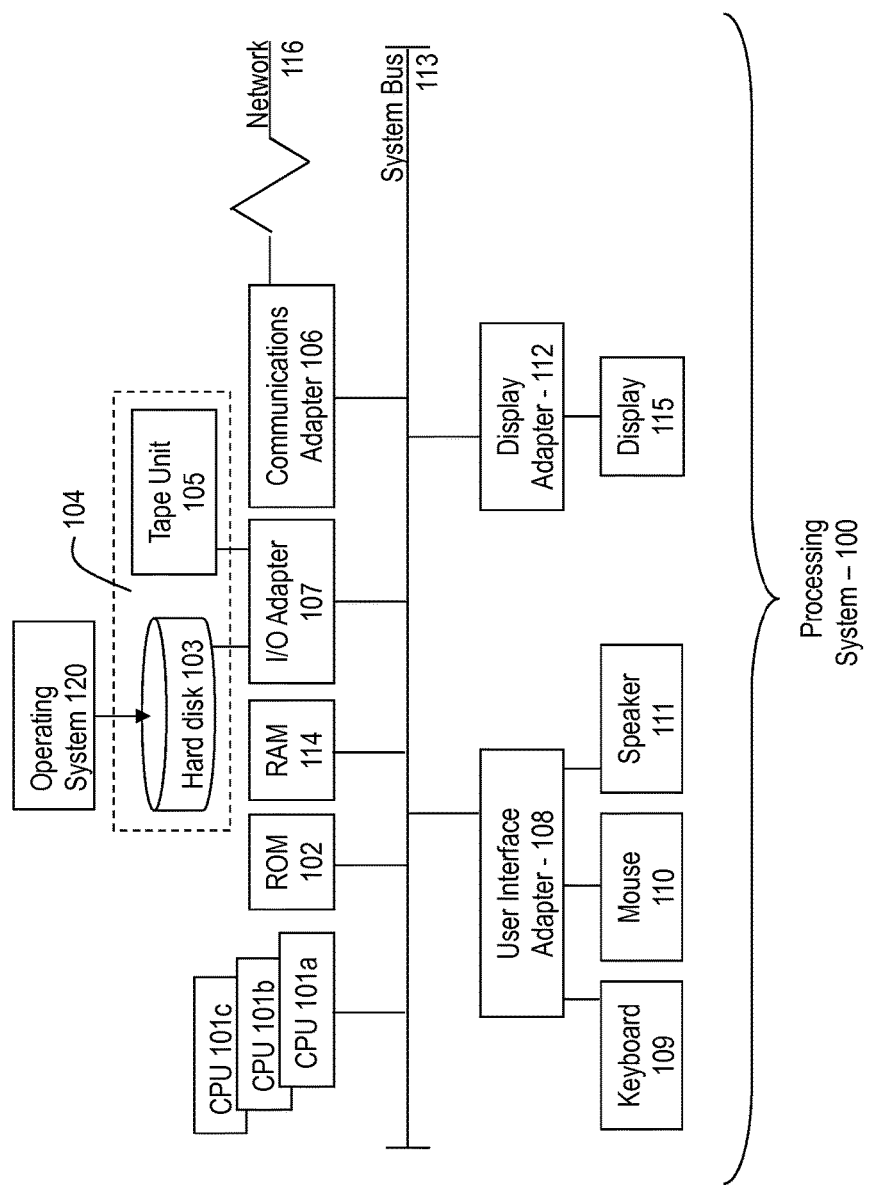
FIG. 1 is a block diagram illustrating one example of a processing system for practice of the teachings herein.

Referring now to FIG. 1, there is shown an embodiment of a processing system 100 for implementing the teachings herein. In this embodiment, the system 100 has one or more central processing units (processors) 101a, 101b, 101c, etc. (collectively or generically referred to as processor(s) 101). In one embodiment, each processor 101 may include a reduced instruction set computer (RISC) microprocessor. Processors 101 are coupled to system memory 114 and various other components via a system bus 113. Read only memory (ROM) 102 is coupled to the system bus 113 and may include a basic input/output system (BIOS), which controls certain basic functions of system 100.

FIG. 1 further depicts an input/output (I/O) adapter 107 and a network adapter 106 coupled to the system bus 113. I/O adapter 107 may be a small computer system interface (SCSI) adapter that communicates with a hard disk 103 and/or tape storage drive 105 or any other similar component. I/O adapter 107, hard disk 103, and tape storage device 105 are collectively referred to herein as mass storage 104. Operating system 120 for execution on the processing system 100 may be stored in mass storage 104. A network adapter 106 interconnects bus 113 with an outside network 116 enabling data processing system 100 to communicate with other such systems. A screen (e.g., a display monitor) 115 is connected to system bus 113 by display adaptor 112, which may include a graphics adapter to improve the performance of graphics intensive applications and a video controller. In one embodiment, adapters 107, 106, and 112 may be connected to one or more I/O busses that are connected to system bus 113 via an intermediate bus bridge (not shown). Suitable I/O buses for connecting peripheral devices such as hard disk controllers, network adapters, and graphics adapters typically include common protocols, such as the Peripheral Component Interconnect (PCI). Additional input/output devices are shown as connected to system bus 113 via user interface adapter 108 and display adapter 112. A keyboard 109, mouse 110, and speaker 111 all interconnected to bus 113 via user interface adapter 108, which may include, for example, a Super I/O chip integrating multiple device adapters into a single integrated circuit.

Thus, as configured in FIG. 1, the system 100 includes processing capability in the form of processors 101, storage capability including system memory 114 and mass storage 104, input means such as keyboard 109 and mouse 110, and output capability including speaker 111 and display 115. In one embodiment, a portion of system memory 114 and mass storage 104 collectively store an operating system such as the AIX® operating system from IBM Corporation to coordinate the functions of the various components shown in FIG. 1.

Figure 2:
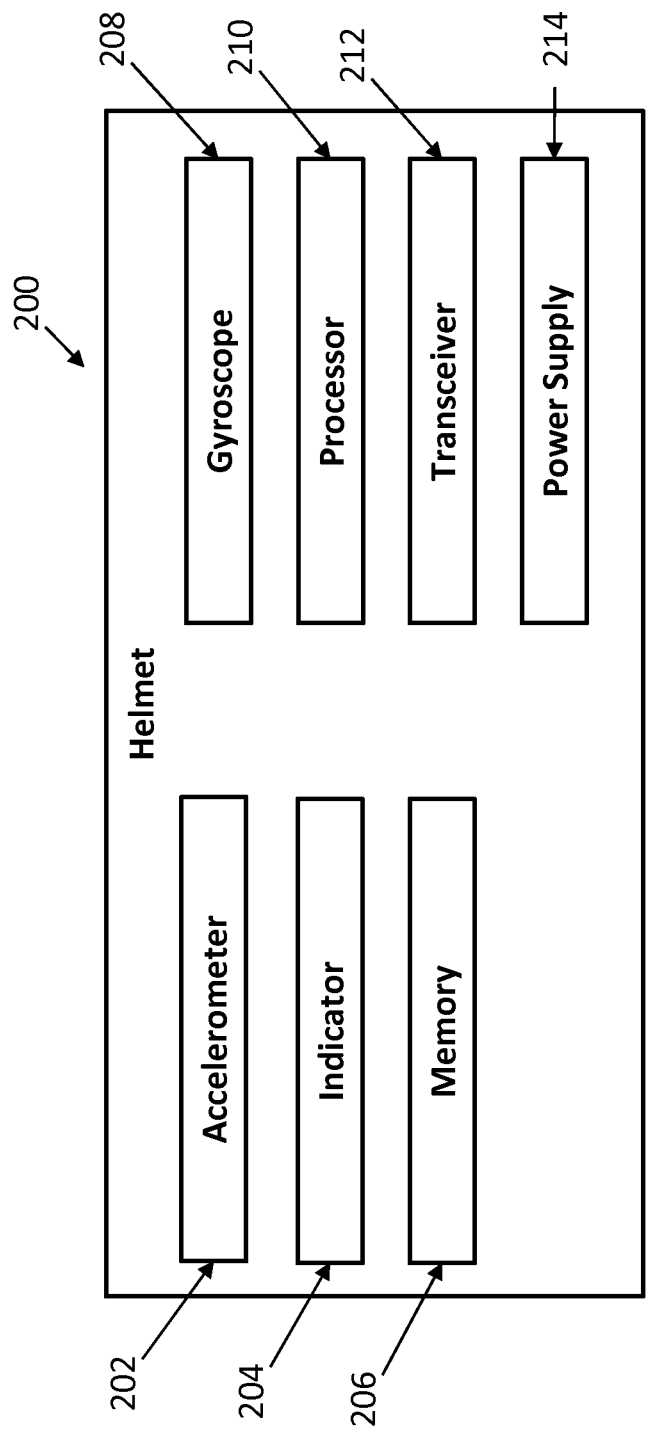
FIG. 2 is a block diagram illustrating a helmet in accordance with an exemplary embodiment.

Referring to FIG. 2, a block diagram illustrating a helmet 200 in accordance with an exemplary embodiment is shown. The term "helmet" may include, but is not intended to be limited to, a football helmet, a motorcycle helmet or the like. In exemplary embodiments, the helmet 200 includes one or more of the following: an accelerometer 202, an indicator 204, a memory 206, a gyroscope 208, a processor 210, a transceiver 212, and a power supply 214. In exemplary embodiments, the power supply 214 may be a battery configured to provide power to one or more of the accelerometer 202, the indicator 204, the memory 206, the gyroscope 208, the processor 210, and the transceiver 212.

In one embodiment, the processor 210 is configured to receive an output from one or more of the accelerometer 202 and the gyroscope 208 and store data in memory 206 about impacts experienced by helmet 200. In addition, the processor 210 is configured to analyze the data stored in the memory 206 and to calculate a cumulative concussion score. The processor 210 is further configured to control the indictor 204 based on the calculated cumulative concussion score. For example, the indicator 204 may include one or more LEDs that are selectively activated by the processor 210 based on the cumulative concussion score.

In exemplary embodiments, the processor 210 is configured to monitor data received from the accelerometer 202 and the gyroscope 208 and to transmit an alert if the data received indicates that the helmet 200 has suffered a severe impact. As used herein, the term severe impact is an impact sufficient to cause a traumatic brain injury. The processor 210 may compare the data received from the accelerometer 202 and the gyroscope to one or more threshold values for determining if an impact experienced by the helmet 200 is severe. The processor 210 stores all of the data received from the accelerometer 202 and the gyroscope 208 in the memory 206.

In exemplary embodiments, the processor 210 of the helmet 200 is configured to analyze the data stored in the memory 206 corresponding to impacts that the helmet, and therefore its user, has experienced over time. In particular, the data stored in the memory 206 corresponds to all impacts that the helmet 200 has experienced during a given time period and not only data corresponding to impacts determined to be severe. The processor 210 analyzes the data stored in the memory 206 and calculates a cumulative concussion score that indicates the severity of the cumulative effects of the non-severe impacts experienced by the user of the helmet. In one embodiment, the cumulative concussion score may range from zero to one, with zero indicating the amount risk for brain injury due to the cumulative effects of the non-severe impacts and with one indicating the highest amount of risk for brain injury due to the cumulative effects of the non-severe impacts. In exemplary embodiments, the indicator 204 includes a plurality of LEDs and the processor 210 selectively activates one or more of the LEDs based on the cumulative concussion score. For example, the indicator 204 may use a color of the LEDs to indicate the cumulative concussion score or the indicator 204 may use the number of illuminated LEDs to indicate the cumulative concussion score.

In exemplary embodiments, the processor 210 may be configured to transmit the cumulative concussion score to a separate processing system that can be used to monitor the cumulative concussion score of multiple individuals. The processor 210 may transmit the cumulative concussion score periodically or upon the cumulative concussion score surpassing one or more threshold levels.

In addition, the processor 210 may be configured to receive a medical history of the user, which can be utilized in calculating the cumulative concussion score of the user. For example, a user that has suffered multiple concussions may be more sensitive to less than severe impacts than users that have not previously suffered a concussion. As a result, the processor 210 may utilize different functions for calculating the cumulative concussion score of different users based on the medical history of the user. Likewise, the processor 210 may use different thresholds for triggering alerts based on the medical history.

Figure 3:
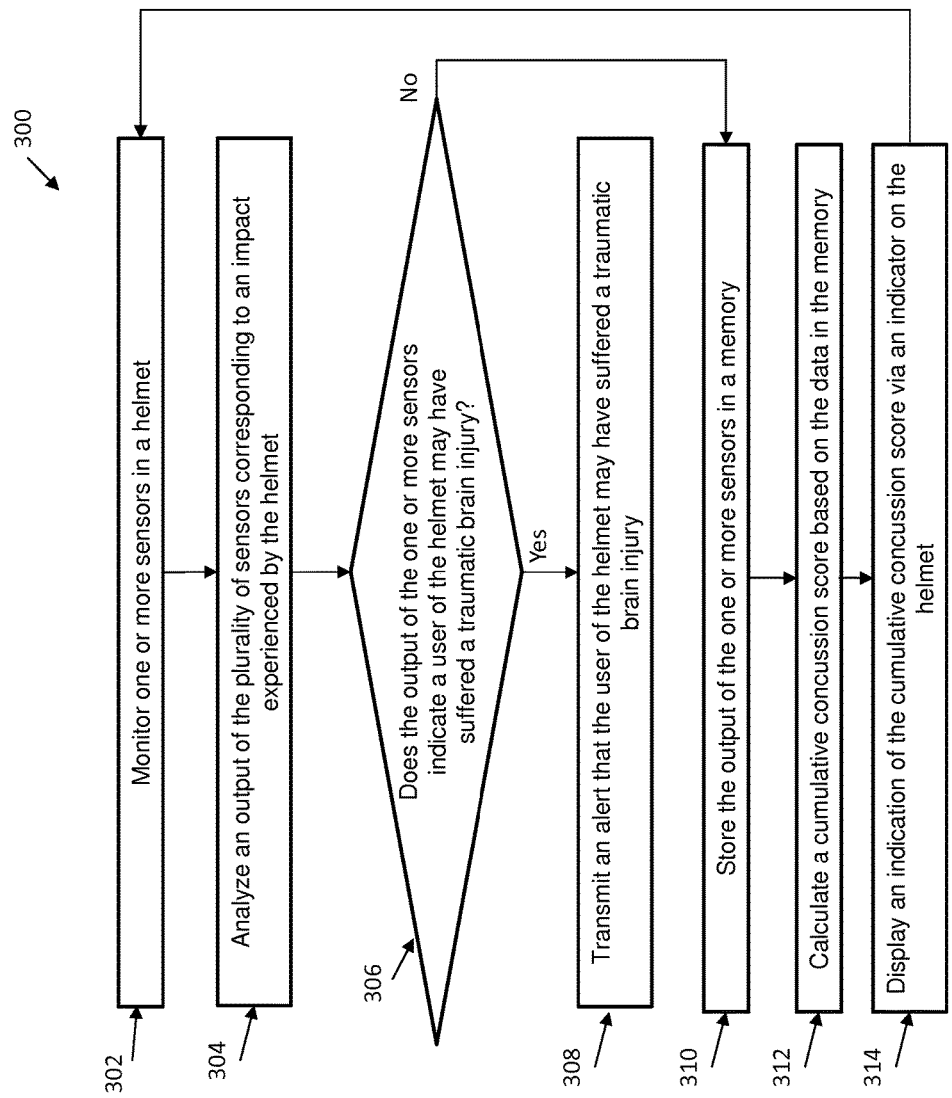
FIG. 3 is a flow diagram of a method for monitoring a user for cumulative concussions in accordance with an exemplary embodiment.

Referring now to FIG. 3, a flow diagram of a method 300 for monitoring a user of a helmet for cumulative concussions in accordance with an exemplary embodiment is shown. As shown at block 302, the method 300 includes monitoring a plurality of sensors in the helmet. In exemplary embodiments, the plurality of sensors includes an accelerometer and a gyroscope. Next, as shown at block 304, the method 300 includes analyzing an output of the plurality of sensors corresponding to an impact experienced by the helmet. In exemplary embodiments, analyzing the output of the plurality of sensors may include comparing the output of the plurality of sensors to one or more stored profiles corresponding to normal measurements from each of the plurality of sensors or to one or more thresholds for each of the plurality of sensors.

As shown at decision block 306, the method 300 includes determining if the output of the plurality of sensors indicates a user of the helmet may have suffered a traumatic brain injury. If the output of the plurality of sensors indicates that the user of the helmet may have suffered a traumatic brain injury, the method 300 proceeds to block 308 and includes transmitting an alert that the user of the helmet may have suffered a traumatic brain injury. Otherwise, the method 300 proceeds to block 310 and stores the output of the plurality of sensors in a memory. Next, as shown at block 312, the method 300 includes calculating a cumulative concussion score based on the data in the memory. In exemplary embodiments, the cumulative concussion score may also be based on a medical history of the user. The method 300 also includes displaying an indication of the cumulative concussion score via an indicator on the helmet. In exemplary embodiments, the indicator includes a plurality of lights which are selectively activated based on the cumulative concussion score. For example, the indicator may use different color lights to indicate the cumulative concussion score or the indicator may use the number of illuminated lights to indicate the cumulative concussion score. Once the method 300 updates the indicator based on the cumulative concussion score, the method 300 returns to block 302 and continues to monitor the output of the plurality of sensors.

Figure 4:
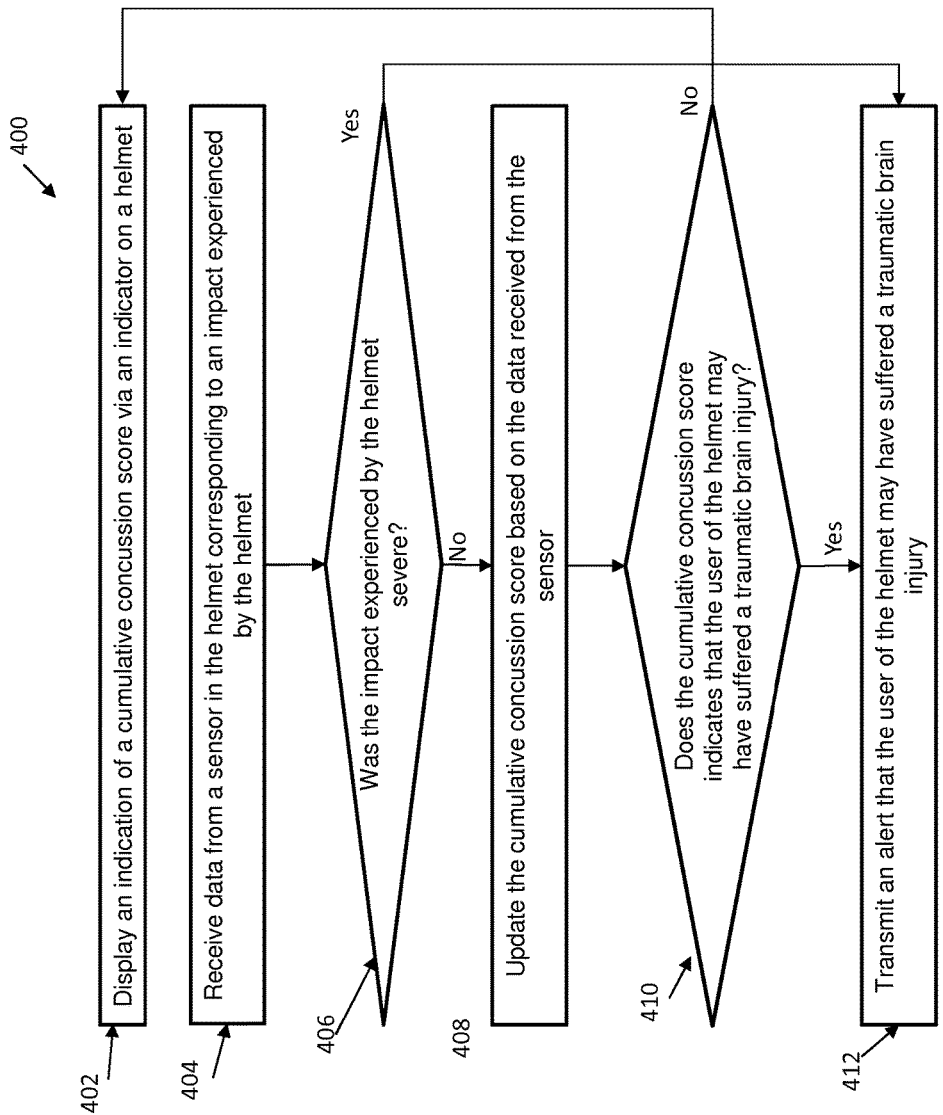
FIG. 4 is a flow diagram of another method for monitoring a user for cumulative concussions in accordance with an exemplary embodiment.

Referring now to FIG. 4, a flow diagram of a method 400 for monitoring a user for brain injuries in accordance with an exemplary embodiment is shown. As shown at block 402, the method 400 includes displaying an indication of a cumulative concussion score via an indicator on a helmet. In exemplary embodiments, the indicator includes a plurality of lights which are selectively activated based on the cumulative concussion score. For example, the indicator may use different color lights to indicate the cumulative concussion score or the indicator may use the number of illuminated lights to indicate the cumulative concussion score. Next, as shown at block 404, the method 400 includes receiving data from a sensor in the helmet corresponding to an impact experienced by the helmet. The method 400 also includes determining if the impacts experienced by the helmet severe, as shown at decision block 406. In exemplary embodiments, determining if the impact experienced by the helmet severe may include determining if the data received from the sensor exceeds a threshold level. If the impact experienced by the helmet severe, the method 400 proceeds to block 412 and includes transmitting an alert that the user of the helmet may have suffered a traumatic brain injury. Otherwise, the method 400 proceeds to block 408 and includes updating the cumulative concussion score based on the data received from the sensor. Next, as shown at decision block 410, the method 400 includes determining if the cumulative concussion score indicates that the user of the helmet may have suffered a traumatic brain injury. If the cumulative concussion score indicates that the user of the helmet may have suffered a traumatic brain injury, the method 400 proceeds to block 412 and includes transmitting an alert that the user of the helmet may have suffered a traumatic brain injury. Otherwise, the method 400 returns to block 402 and updates the cumulative concussion score displayed via an indicator on a helmet.

In exemplary embodiments, the alerts transmitted by the helmet that the user of the helmet may have suffered a traumatic brain injury may include, but is not limited to, one or more of: an identification of the user; the cumulative concussion score of the user; data regarding any impacts experienced by the user in a predefined time period prior to the transmission; and an indication of a confidence level associated with indication that the user may have suffered a traumatic brain injury.

Figure 5:
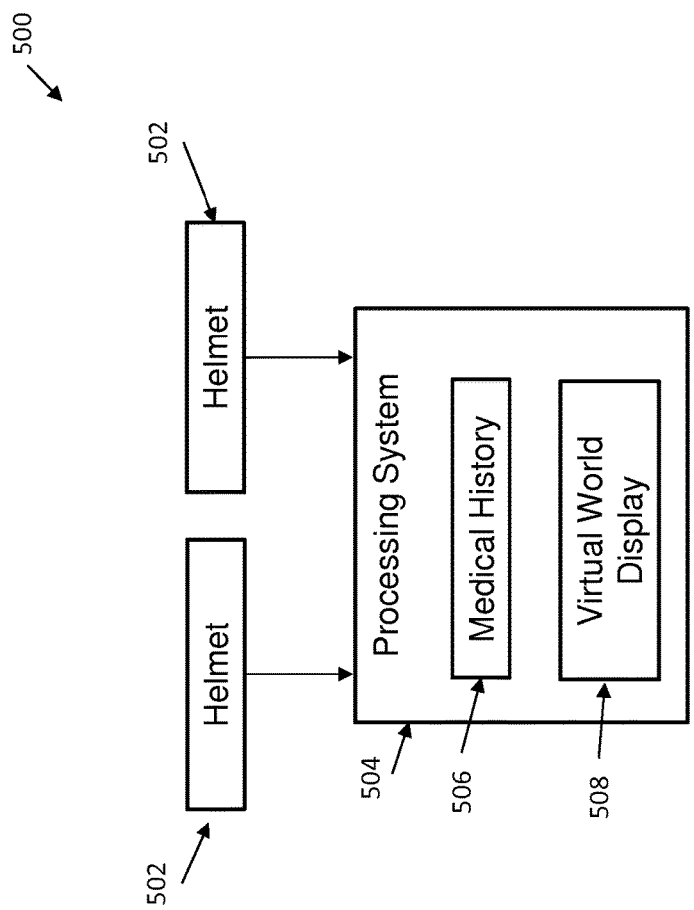
FIG. 5 is a block diagram illustrating a system for monitoring helmets in accordance with an exemplary embodiment.

Referring now to FIG. 5, a block diagram illustrating a system 500 for monitoring users of helmets for traumatic brain injuries in accordance with an exemplary embodiment is shown. As illustrated, the system 500 includes one or more helmets 502, such as the one shown and described above with reference to FIG. 2, and a processing system 504, such as the one shown and described above with reference to FIG. 1. The processing system 504 is configured to communicate with the helmets 502 and is also configured to store the medical history 506 of the users of the helmets 502. In exemplary embodiments, the medical history 506 of the users of the helmets 502 may be used by the helmet in calculating the cumulative concussion score and in determining the threshold level for a severe impact. In addition, the processing system 504 may include a virtual world display 508 that is configured to provide a display a real-time status of each of the users of the helmets. In exemplary embodiments, the status may include, the cumulative concussion score of each user, any indications that the user may have suffered a traumatic brain injury, a duration of play of the user, a duration that the user has been in the current category of play, or the like.

In exemplary embodiments, the user's history of collision or medical concerns may be used to determine a traumatic brain injury risk assessment, either by the embedded processor or the separate processing system. In addition, the helmet may be configured to provide a real-time feed of the user's cognitive state to increase the confidence level of the need for a particular alert or indication. In exemplary embodiments, an aggregate indication may be used to summarize an overall state of a group of players. This may also help to potentially identify area of risk in the dynamics of player-player interaction, overly aggressive players, playing field conditions, etc. In exemplary embodiments, an automatic feed from a user's history of collision or medical concerns may also be provided to a processor of the helmet in order to update an impact risk model for each category of play. In addition, the processing system 504 may receive a real-time feed of the user's cognitive state, which can be used to update the risk models used by the helmets. The risk models may also be sent to the virtual world display 508 of the game and players, which allows the sports staff health professionals to visualize the nature of potential problems.

In exemplary embodiments, a virtual world representation includes a graphical representation of the field of play in which each player is represented by an avatar. A cumulative concussion score may be visualized on the avatar's helmet or body (e.g. by changes in size, color, texture, text labels on the avatar, icons on the avatar) and also by the avatar's movements (e.g. the avatar may become slower, jittery, etc.) in the virtual world representation. In exemplary embodiments, clicking on the causes the virtual world representation to display additional information to the user, such as data relating to the time and severity of past concussions.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method for monitoring a user of a helmet for cumulative concussions, the method comprising:
    monitoring one or more sensors in the helmet;
    receiving, by a processor in the helmet, an output from the one or more sensors corresponding to an impact experienced by the helmet;

determining, by the processor in the helmet, whether the impact is a severe impact by comparing the output of the one or more sensors with one or more thresholds that are based on a medical history of the user;

based on a determination that the impact experienced by the helmet is a severe impact, transmitting, by the helmet to a separate processing system, an alert that the user of the helmet may have suffered a traumatic brain injury;

calculating, by the processor in the helmet, a cumulative concussion score by summing the output of the one or more sensors corresponding to impacts that are determined to be non-severe;

periodically transmitting the cumulative concussion by the helmet to the separate processing system;

displaying an indication of the cumulative concussion score via an indicator on the helmet;

displaying, on the separate processing system, a virtual world display of a game including an avatar representing the user of the helmet in which a movement of the avatar becomes slower as the cumulative concussion score of the user increases.

2. The method of claim 1, wherein the indicator includes a plurality of lights and wherein the indication of the score is displayed by selectively illuminating one or more of the plurality of lights.

3. The method of claim 2, wherein each of the plurality of lights are of different colors.

4. The method of claim 1, wherein the method further comprises:

determining if the cumulative concussion score exceeds a threshold level; and transmitting an alert that the user of the helmet may have suffered a traumatic brain injury.

* * * * *